(12) United States Patent
Muse et al.

(10) Patent No.: US 11,200,970 B2
(45) Date of Patent: Dec. 14, 2021

(54) SYSTEMS AND METHODS FOR SHARING RECORDED MEDICAL DATA WITH AUTHORIZED USERS

(71) Applicant: Optum, Inc., Minnetonka, MN (US)

(72) Inventors: Jon Kevin Muse, Thompson Station, TN (US); Gregory J. Boss, Saginaw, MI (US); Rama S. Ravindranathan, Basking Ridge, NJ (US)

(73) Assignee: Optum, Inc., Minnetonka, MN (US)

( * ) Notice: Subject to any disclaimer, the term of this patent is extended or adjusted under 35 U.S.C. 154(b) by 0 days.

(21) Appl. No.: 16/780,184

(22) Filed: Feb. 3, 2020

(65) Prior Publication Data

US 2021/0241869 A1 Aug. 5, 2021

(51) Int. Cl.
*G16H 10/60* (2018.01)
*H04L 29/06* (2006.01)
*G06F 9/54* (2006.01)
*G06F 21/31* (2013.01)

(52) U.S. Cl.
CPC ............. *G16H 10/60* (2018.01); *G06F 9/542* (2013.01); *G06F 21/31* (2013.01); *H04L 63/04* (2013.01); *H04L 63/08* (2013.01)

(58) Field of Classification Search
CPC ......... G06F 9/542; G06F 21/31; G16H 10/60; H04L 63/04; H04L 63/08
See application file for complete search history.

(56) References Cited

U.S. PATENT DOCUMENTS

| | | | |
|---|---|---|---|
| 7,370,349 B2 | 5/2008 | Holvey et al. | |
| 10,195,513 B2 | 2/2019 | Tran et al. | |
| 10,841,286 B1* | 11/2020 | Davidovics | H04L 9/3247 |
| 2003/0074564 A1 | 4/2003 | Peterson | |
| 2010/0082370 A1 | 4/2010 | Frederick et al. | |
| 2010/0094658 A1 | 4/2010 | Mok et al. | |
| 2010/0102123 A1* | 4/2010 | Skowronek | G06Q 20/20 235/380 |
| 2010/0299155 A1 | 11/2010 | Findlay et al. | |
| 2017/0360313 A1* | 12/2017 | Baek | A61B 5/02108 |
| 2018/0085069 A1* | 3/2018 | Murali | A61B 5/11 |
| 2018/0368762 A1* | 12/2018 | Cetingul | A61B 5/0428 |
| 2019/0371440 A1* | 12/2019 | Parvaneh | H04W 4/025 |
| 2020/0020428 A1* | 1/2020 | Avery | G16H 10/60 |

* cited by examiner

*Primary Examiner* — Gil H. Lee
(74) *Attorney, Agent, or Firm* — Alston & Bird LLP

(57) ABSTRACT

Systems and methods are configured for maintaining identifying data of a first user in association with a personal device of the first user; maintaining a rolling recording of medical data generated at the personal device of the first user, wherein the rolling recording encompasses data generated during a defined duration of time; receiving a request to access the medical data from a second device, wherein the request comprises authorization credentials associated with the second device; and upon verification that the authorization credentials are associated with an authorized user, providing, to the second device, access to the rolling recording of medical data generated at the personal device of the first user.

17 Claims, 7 Drawing Sheets

SYSTEMS AND METHODS FOR SHARING RECORDED MEDICAL DATA WITH AUTHORIZED USERS

BACKGROUND

Providing healthcare to a patient, such as in an emergency setting, is often facilitated by the receipt of relevant health information about the patient. Medical professionals often obtain this relevant health information by asking the patient some questions about recent symptoms, conditions, and activities. However, if the patient is unconscious, delirious, or otherwise incapacitated, such as during many common emergency healthcare scenarios, the medical professional has limited options for obtaining any health information about the patient. For example, the "In Case of Emergency" (ICE) feature on a smartphone stores static information and limited to information such as name, emergency contacts, allergies, and medications. Options for obtaining recent medical information are limited, and generally encompass the above-noted options for asking questions of a patient. However, even these options have limitations, as patients may not be completely truthful, or patients may not remember all relevant information. Accordingly, a need exists for systems and methods enabling a person to convey relevant health information to medical personnel during emergency scenarios. Various embodiments of the present invention address the shortcomings of the current medical data obtaining systems and are directed to various techniques for efficiently and reliably accessing recent medical data of the person.

BRIEF SUMMARY

In accordance with one aspect, a method is provided. In one embodiment, the method comprises maintaining a rolling recording of personal data generated at a personal device of a first user, wherein the rolling recording encompasses data generated during a defined duration of time; receiving a request to access the personal data from a second device, wherein the request comprises authorization credentials associated with the second device; and upon verification that the authorization credentials are associated with an authorized user, providing, to the second device, access to the rolling recording of personal data generated at the personal device of the first user. As just one example, the first device is associated with a first user, e.g., a patient. As just another example, the second device is associated with a medical practitioner, e.g., an EMT, a nurse.

In accordance with another aspect, a computer program product for sharing data in association with a personal device of a first user is provided. The computer program product for sharing data in association with a personal device of a first user comprises at least one non-transitory computer-readable storage medium having computer-readable program code portions stored therein, the computer-readable program code portions configured to: maintain a rolling recording of personal data generated at a personal device of a first user, wherein the rolling recording encompasses data generated during a defined duration of time; receive a request to access the personal data from a second device, wherein the request comprises authorization credentials associated with the second device; and upon verification that the authorization credentials are associated with an authorized user, provide, to the second device, access to the rolling recording of personal data generated at the personal device of the first user.

In accordance with another aspect, an apparatus for sharing data in association with a personal device of a first user is provided. The apparatus for sharing data in association with a personal device of a first user comprises at least one processor and at least one memory including program code, the at least one memory and the program code configured to, with the processor, cause the apparatus to at least: maintain a rolling recording of personal data generated at a personal device of a first user, wherein the rolling recording encompasses data generated during a defined duration of time; receive a request to access the personal data from a second device, wherein the request comprises authorization credentials associated with the second device; and upon verification that the authorization credentials are associated with an authorized user, provide, to the second device, access to the rolling recording of personal data generated at the personal device of the first user.

BRIEF DESCRIPTION OF THE DRAWINGS

Figure 1:
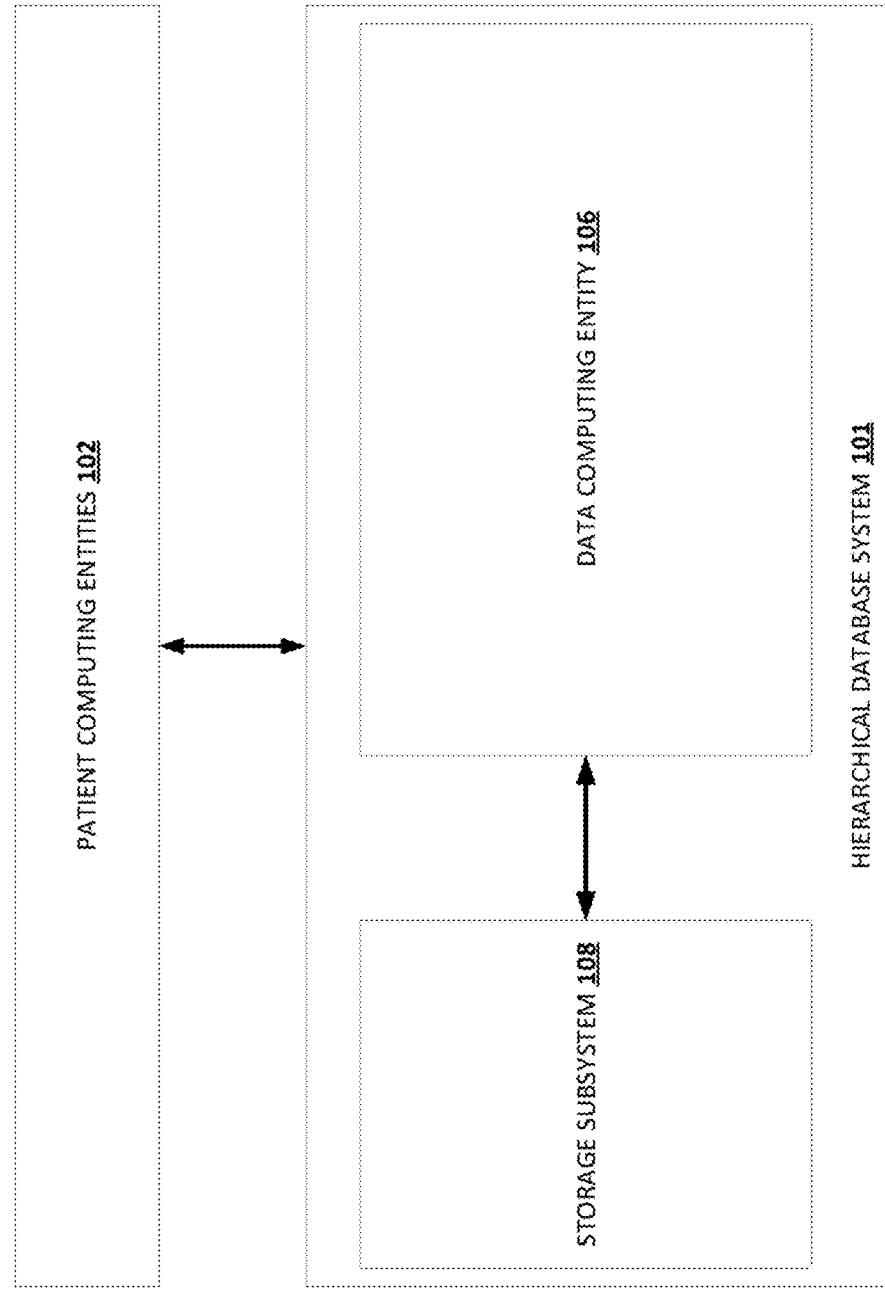

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
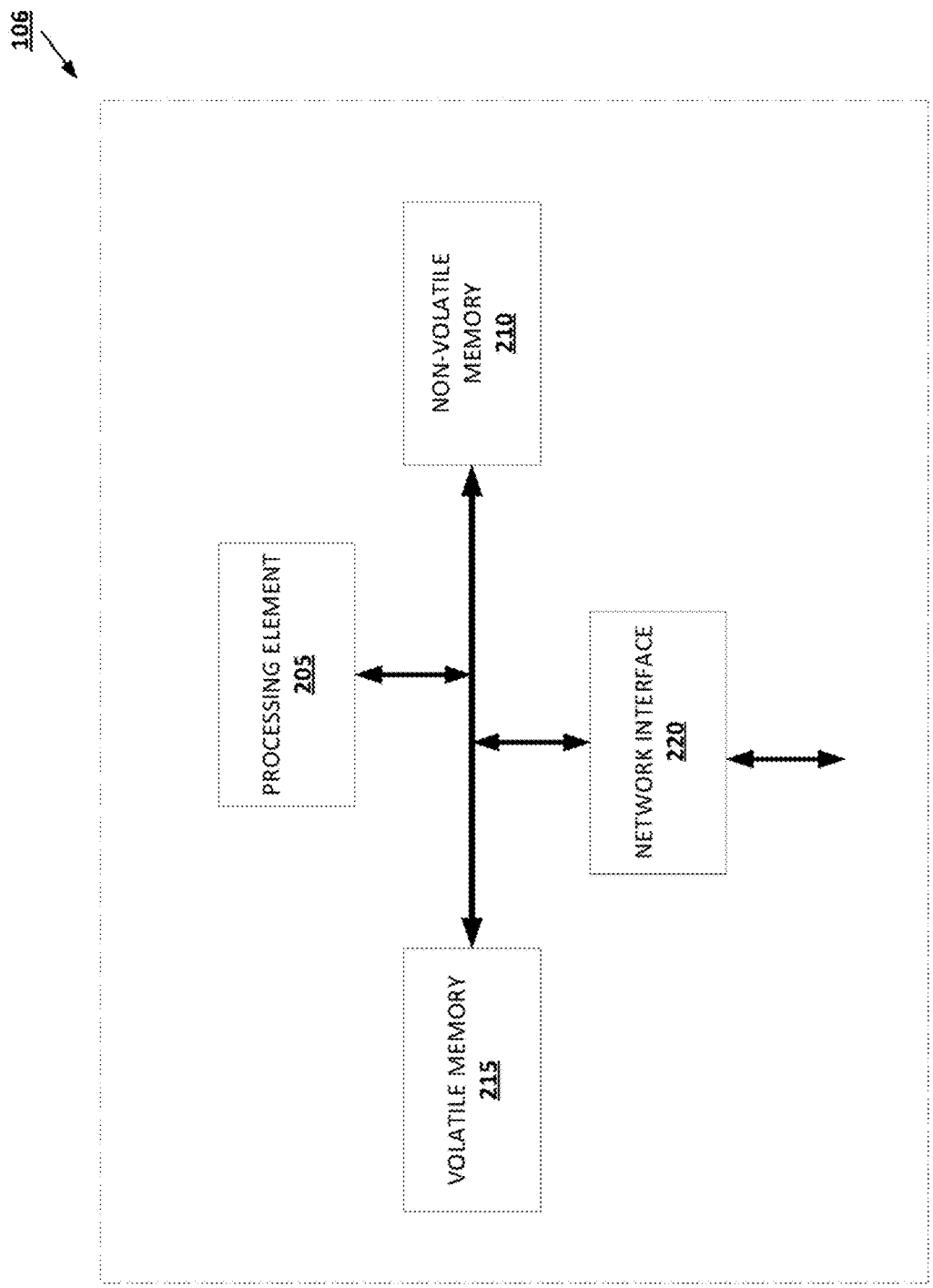

FIG. 2 provides an example data computing entity, in accordance with some embodiments discussed herein.

Figure 3:
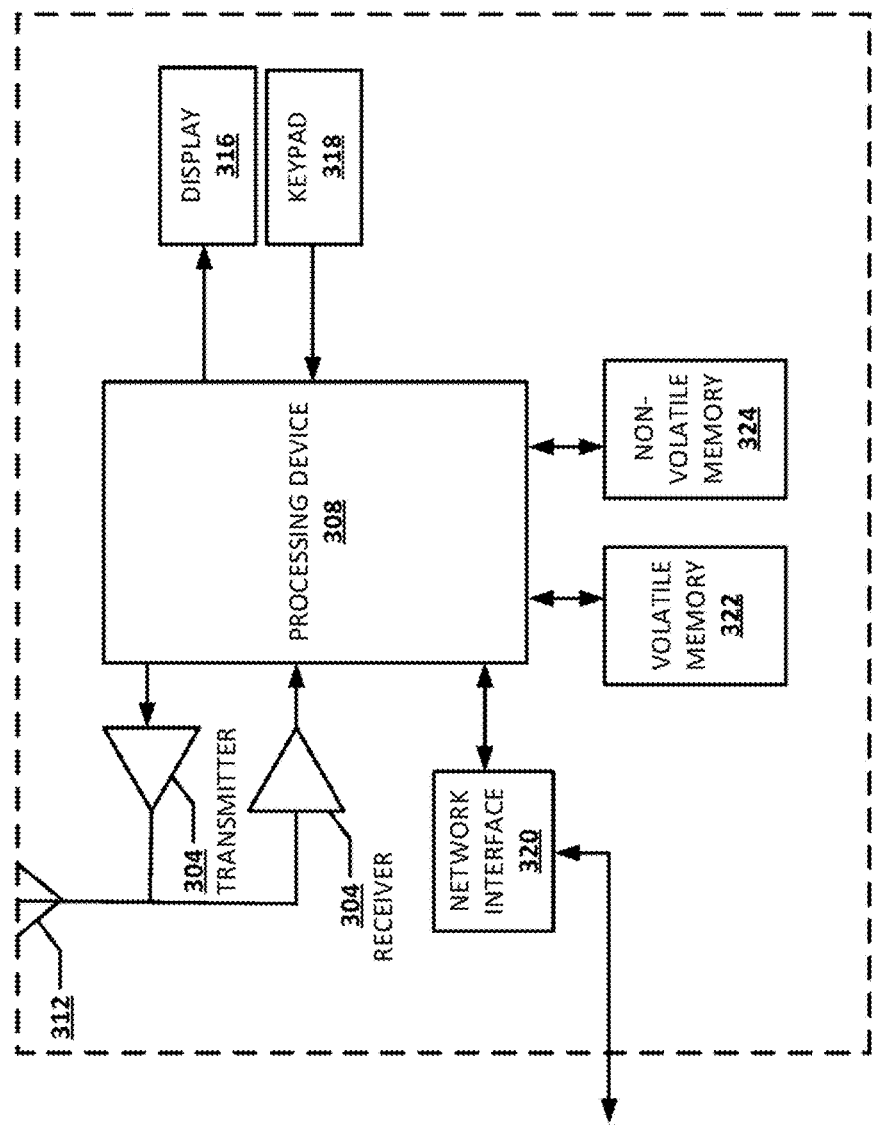

FIG. 3 provides an example patient computing entity, in accordance with some embodiments discussed herein.

Figure 4:
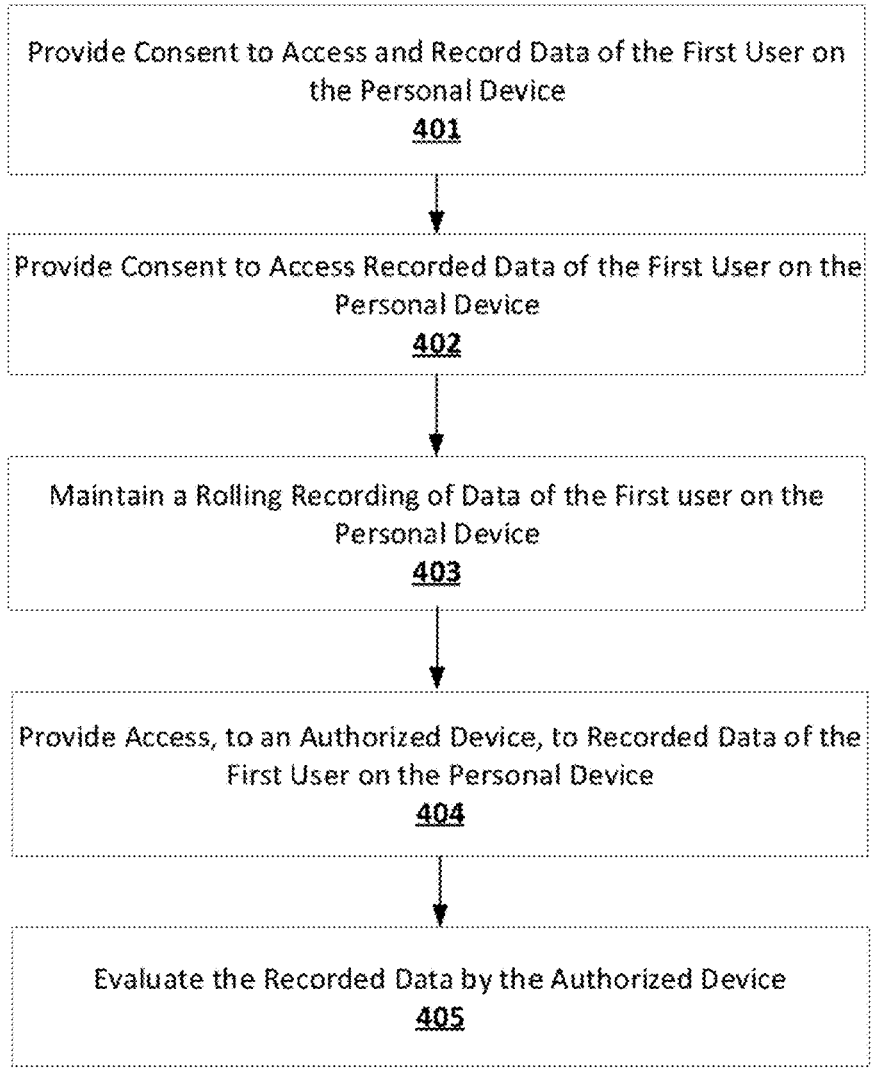

FIG. 4 provides an example process for sharing data in association with a personal device of a first user, in accordance with some embodiments discussed herein.

Figure 5:
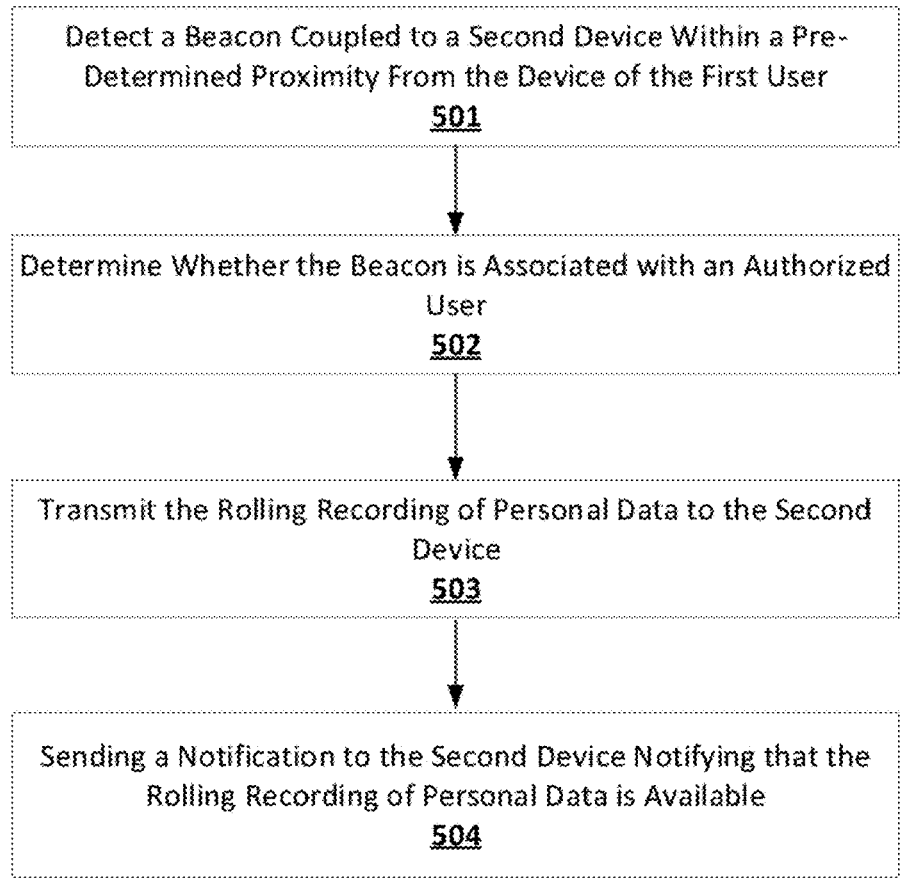

FIG. 5 provides an example process for receiving a request to access the personal data from a second device, in accordance with some embodiments discussed herein.

Figure 6:
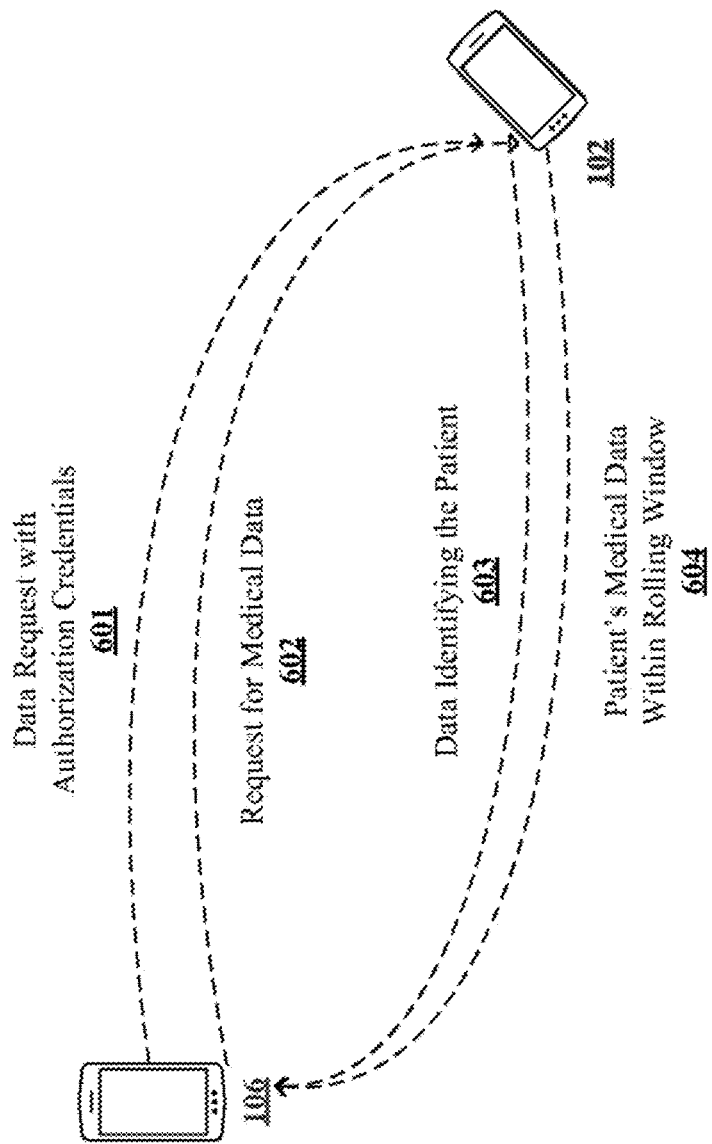

FIG. 6 provides an operational example of sharing medical data between a personal device of a first user and a second device, in accordance with some embodiments discussed herein.

Figure 7A:
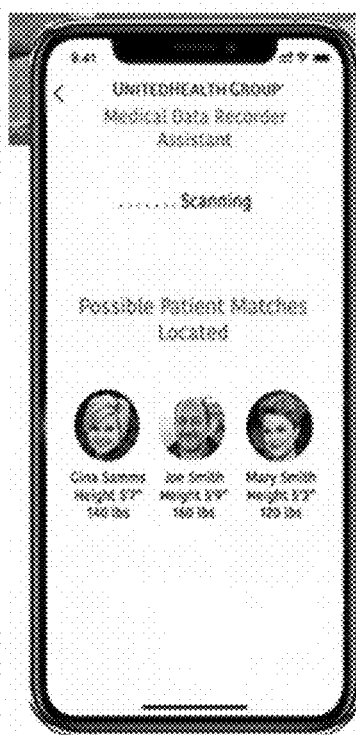
Figure 7B:
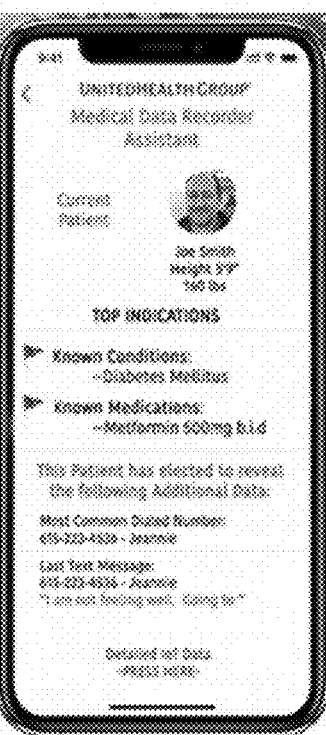
Figure 7C:
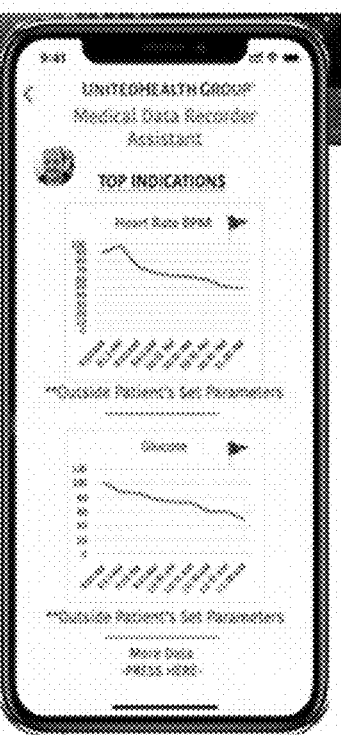

FIGS. 7A-7C provide an operational example of a user interface on a personal device of an authorized medical personnel, in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview

Certain embodiments are directed to systems and methods for sharing recorded medical data with authorized users.

Some embodiments provide a rolling window of medical, personal, and environmental information that is objective and relevant to a medical professional. Various embodiments enable methodologies for obtaining data regarding multiple patients and selecting an appropriate data set corresponding to a particular patient. A patient's personal device(s) collects a rolling window of data regarding the patient's recent activities (e.g., from a most-recent time period having a fixed duration ending at a present time) and stores that data in association with identifying data (e.g., static identifying data) of the patient. In various embodiments, the static identifying data may include name, date of birth, static health information, and In Case of Emergency (ICE) information. The recorded data is associated with patient-specified privacy preferences regarding who can access the data. To that end, the patient can opt-in to data gathering and can establish preferences of types of data to be collected.

Prior to configurations (e.g., a patient's smartphone) collecting patient's data, the patient installs a corresponding application designated to record and/or interact with devices and/or other applications configured to record medical data, i.e., medical data recorder, of the patient on his/her personal device. In certain embodiments, the application is configured to receive user input enabling the patient to specify medical data recorder application settings. The application may additionally be configured to receive user input specifying at least one authorized person to access the recorded data. The authorized persons may include specifically identified persons, such as family members, friends, caretakers, and/or the like, or persons having identified credentials, such as emergency personnel having medical licenses, employee identifications with hospitals or other medical-related entities, and/or the like, such as an EMT. For example, an EMT may have appropriate credentials, as established within a corresponding application stored on the EMT's smartphone/device, enabling access to identifying data, such as photos or avatars of potential patients near him/her, such that the EMT is enabled to provide user input selecting a specific individual person in need of medical attention, and to view the specific individual person's recorded medical data in the specified rolling window.

Once the patient grants access to the application (e.g., by providing user input to the application granting access to the application to record medical data), the application begins tracking and recording specified data of the patient. Various embodiments provide access to the application to various data types, for example, the application may access one or more of: various sensors, e.g., accelerometers, GPS, and/or the like; settings of the patient's personal device, and/or applications, e.g., heart rate measurement applications, on the patient's device (or otherwise accessible to the patient's device) to obtain and record desired data. In certain embodiments, the application may comprise modules configured to (e.g., trained via machine learning to) analyze events in the recorded data that can aid with medical diagnosis and/or to flag those events for easy viewing by medical personnel (or other users having access to the patient's data).

During an emergency scenario, medical personnel, or other authorized persons, can access the recorded data of the patient via their own personal device based on a determination that the person is sufficiently close to the patient, e.g., within a range of direct device-to-device transmission, or within a geofenced area having a defined diameter surrounding the patient (e.g., centered at the patient's personal device), and a determination that the person is authorized to access the recorded data. Configurations may synchronize recorded data into medical records accessible to the medical personnel. In certain embodiments, systems and/or methods may further prioritize medically necessary events and make them available to the medical personnel. The authorized persons may select what types of recorded data they desire to access, what time slots of the rolling window they want to focus on, and whether they would prefer to see two or more types of recorded data simultaneously, and/or the like (e.g., via user-specific settings provided to an appropriate application executing on the authorized personnel's device). Therefore, various embodiments ensure that relevant medical information of the patient is provided to the medical personnel's personal device and is organized for display via an application and user-specific preferences.

1. Technical Problem

Recent and/or relevant medical data associated with a patient in an emergency may not be readily available, such as in scenarios in which a patient is incapacitated or otherwise incapable of communicating with a care provider (e.g., a medical provider). Knowledge about most recent medical data and conditions of the patient can facilitate diagnosis and treatment of the patient. However, some current solutions, such as the ICE feature on a phone, merely include static information and are limited to information such as name, emergency contacts, allergies, medications, and/or other static information that may become stale if not manually updated. Other currently known solutions to obtain recent medical information are limited to obtain relevant data from the patient, and even in this case the responses are subjective, inaccurate, incomplete, or otherwise untrustworthy. Moreover, current data gathering techniques are not limited to a rolling window and include all available data for the user. Further, such data gathering techniques usually only provide the end user a warning. Accordingly, a need exists for systems and methods enabling a person to convey relevant health information to medical personnel during emergency scenarios.

2. Technical Solution

To address the noted technical challenges associated with the availability of medical data in case of emergency, various embodiments of the present invention disclose sharing data in association with a personal device of a patient (e.g., the patient's smartphone, wearable, and/or the like). Such data may comprise objective data collected by one or more sensors associated a personal device, such as Internet of Things (IoT) sensors (e.g., connected heartrate monitors, connected activity trackers, connected temperature (e.g., body temperature and/or ambient temperature), dietary tracking applications of a smartphone, connected altimeters, connected location trackers, and/or the like). In one aspect, disclosed sharing data in association with a personal device of a first user relates to improve validity and accuracy of medical data, and to present a clear picture of the patient's recent conditions. Moreover, such data may be presented in a user (e.g., medical provider)-specified, organized manner, so as to highlight potentially relevant recent medical, environmental, dietary, and/or other events experienced by the patient that may have led to a medical emergency. The availability of reliable recent medical data of the patient helps the medical practitioners in assisting the patient more quickly or accurately. Availability of recent personal medical data in case of emergency is often advantageous for appropriate treatment for urgent medical situations. The present invention discloses a system that collects a limited rolling window of recent medical data and a method to determine when and to whom the medical data will be released.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to: a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1 is a schematic diagram of an example architecture 100 for sharing data generated in association with a personal device of a first user. The architecture 100 includes a data computing entity 106 configured to identify associations between database fields of two or more databases as well as one or more patient computing entities 102 configured to provide data to the data computing entity 106 as well as provide request for cross-database field integration to the data computing entity 106. Upon receiving data from a patient computing entity 102, the data computing entity 106 may store such data in its storage subsystem 108 and utilize the stored data in performing cross-database field integrations. Upon receiving a cross-database field integration request, the data computing entity 106 may perform the cross-database field integration requested by the cross-database field integration and provide integration data (e.g., information about cross-database field associations and/or information about a resulting merged database) to the requesting patient computing entity 102.

In some embodiments, the data computing entity 106 may communicate with at least one of the patient computing entities 102 using one or more communication networks, such as the communication network. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like). In certain embodiments, the data computing entity 106 may operate on and/or in association with processing resources of the patient computing entity 102.

The data computing entity 106 includes the storage subsystem 108. The storage subsystem 108 may include and/or may be associated with one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Data Computing Entity

FIG. 2 provides a schematic of a data computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the data computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the data computing entity 106 may include or be in communication with one or more processing elements 205 (also referred to as processors, processing circuitry, and/or similar terms used herein interchangeably) that communicate with other elements within the data computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the data computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the data computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the data computing entity 106 with the assistance of the processing element 205 and operating system.

As indicated, in one embodiment, the data computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transmit mode (ATM), frame relay, data over cable service interface specification (DOCSIS), or any other wired transmission protocol. Similarly, the data computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the data computing entity 106 may include or be in communication with one or more input elements, such as a keyboard input, a mouse input, a touch screen/display input, motion input, movement input, audio input, pointing device input, joystick input, keypad input, and/or the like. The data computing entity 106 may also include or be in communication with one or more output elements (not shown), such as audio output, video output, screen/display output, motion output, movement output, and/or the like.

As will be appreciated, one or more of the data computing entity's 106 components may be located remotely from other data computing entity 106 components, such as in a distributed system. Furthermore, one or more of the components may be aggregated and additional components performing functions described herein may be included in the data computing entity 106. Thus, the data computing entity 106 can be adapted to accommodate a variety of needs and circumstances.

Exemplary Patient Computing Entity

FIG. 3 provides an illustrative schematic representative of a patient computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Patient computing entities 102 can be operated by various parties. As shown in FIG. 3, the patient computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the patient computing entity 102 may be capable of operating with one or more air interface standards, communication protocols, modulation types, and access types. More particularly, the patient computing entity 102 may operate in accordance with any of a number of wireless communication standards and protocols, such as those described above with regard to the data computing entity 106. In a particular embodiment, the patient computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the patient computing entity 102 may operate in accordance with multiple wired communication standards and protocols, such as those described above with regard to the data computing entity 106 via a network interface 320.

Via these communication standards and protocols, the patient computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The patient computing entity 102 can also download changes, add-ons, and updates, for instance, to its firmware, software (e.g., including executable instructions, applications, program modules), and operating system.

According to one embodiment, the patient computing entity 102 may include location determining aspects, devices, modules, functionalities, and/or similar words used herein interchangeably. For example, the patient computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the patient computing entity's 102 position in connection with a variety of other systems, including cellular towers, Wi-Fi access points, and/or the like. Similarly, the patient computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The patient computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the patient computing entity 102 to interact with and/or cause display of information/data from the data computing entity 106, as described herein. The user input interface can comprise any of a number of devices or interfaces allowing the patient computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the patient computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The patient computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the patient computing entity 102. As indicated, this may include a user application that is resident on the entity or accessible through a browser or other user interface for communicating with the data computing entity 106 and/or various other computing entities.

In another embodiment, the patient computing entity 102 may include one or more components or functionality that are the same or similar to those of the data computing entity 106, as described in greater detail above. As will be recognized, these architectures and descriptions are provided for exemplary purposes only and are not limiting to the various embodiments.

Exemplary Networks

In one embodiment, the networks may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks may have any suitable communication range associated therewith and may include, for example, global networks (e.g., the Internet), MANs, WANs, LANs, or PANs. In addition, the networks may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. Exemplary System Operations

Details regarding various embodiments are described in reference to FIGS. 4-9.

To address the noted technical challenges associated with providing medical data to relevant authorized users (e.g., medical personnel and/or patient-specified individuals) in case of an emergency, various embodiments of the present invention disclose systems and methods for sharing data generated in association with a personal device of a patient. In one aspect, sharing data generated in association with a personal device of a first user relates to improve validity and accuracy of medical data, and to present a clear picture of the patient's recent conditions, for example, by providing objective data collected by one or more sensors in association with the patient's personal device to authorized personnel, and by limiting the data provided to a recent, rolling window of data, so as to limit the provided data to relevant data that may have led to an emergency situation prompting desired access to the data by authorized users. The availability of reliable recent medical data of the patient helps the medical practitioners in assisting the patient more quickly or accurately. Availability of recent personal data in case of emergency is often advantageous for appropriate treatment for urgent medical situations. The present invention discloses a system that collects a limited rolling window of recent personal data and a method to determine when and to whom the personal data will be released.

While health data is dynamic in nature and changes second by second, static ICE data stored on a user's device can become stale, inaccurate and not indicative of current conditions. Thus, although ICE data is informative, it is limited to static data, e.g. name, address, blood type. The present invention provides a rolling window of updated medical, personal, and environmental information that is objective and relevant to a medical professional (or other authorized user, such as other caretakers or other specifically enumerated individuals).

a. Setup of the Data Recorder for a Patient

In some embodiments, a user of a personal device, i.e., the patient operating the patient's personal device, installs an application on his/her personal device. The personal device can be a smartphone, a tablet, a notebook, a wearable device, or any suitable personal device capable of recording and storing data associated with the first user. FIG. 4 provides an example process 400 for sharing data in association with a personal device of a first user, in accordance with some embodiments. The process 400 begins at step/operation 401 when the patient computing entity 102, e.g., the personal device of the first user, receives user input providing consent to the onboard application to access data of the first user on the personal device. In various embodiments, the first user may identify specific data sources (e.g., specific sensors, specific applications, and/or the like) to permit access to the application. For example, the first user may identify a heartrate monitor, a food diary application, and a location tracker associated with the personal device (e.g., onboard the personal device, or accessible to the personal device via one or more communication mechanisms, such as wired communication or wireless communication) as being permitted for access by the application, such that the application is permitted to record data received from each of these sensors. In certain embodiments, the user may be provided with an option to provide a "global" permission to the application, such that the application can record data from any onboard or connected device of the personal device. In other embodiments, the user may be provided with options to specifically tailor the access to the application, such as by selecting individual devices and/or applications (e.g., identifying a subset of all available data sources) for access by the application.

The user may provide such consent during an initial setup of the application, for example, upon an initial launch of the application on the personal device. Moreover, as a part of the setup procedure, a user may establish a username/password combination (or other authentication information) and/or the user may enter established authentication information to gain access to the underlying functionality of the application. The user may additionally setup a user/patient profile, such as comprising identifying information of the user/ patient (e.g., name, date of birth, social security number, health insurance information, and/or the like), ICE information for the patient (e.g., contact information for relatives and/or caretakers of the patient), other static information of the patient (e.g., allergy information indicative of patient allergies, medication information indicative of current medications, and/or the like), and/or the like. The setup process may additionally comprise receipt of user input from the first user providing consent to record accessed data which is generated at the personal device. In some embodiments, the patient computing entity 102 provides consent within the application, e.g., an application associated with a healthcare provider, to record data of the first user. Alternatively, the patient computing entity 102 provides consent to record data within a webpage associated with the healthcare provider and associated with a patient profile (or other data configured to link the provided consent to the patient's personal device). The first user determines which types of data can be accessed and recorded by the application. To that end, in some embodiments, the patient computing entity 102 selects one or more types of data and provides consent to record the one or more types of data. The data accessed and recorded would be limited to the one or more types of data and no further data is accessed and recorded. For example, the first user may consent to access and record incoming and/or outgoing phone calls, or text messages of the first user, but not his/her emails. In such embodiments, the application, i.e., the data computing entity 106, does not access and record other data or applications on the personal device of the first user such as his/her personal emails.

In some embodiments, the patient computing entity 102 authorizes the data computing entity 106 to obtain data from sensors or applications on the patient computing entity 102 (e.g., by transmitting data from the patient computing entity 102 to the data computing entity 106 for storage within a database). In some embodiments, the patient computing entity 102 provides consent to access data obtained from an accelerometer or a pedometer of the personal device, for example, based at least in part on received user input indicative of the provided consent. In some embodiments, the patient computing entity 102 provides consent to access data of body temperature of the first user from the personal device (and/or ambient temperature), for example, based at least in part on received user input indicative of the provided consent. Alternatively, the patient computing entity 102 provides consent to access data of heart rate or blood pressure of the first user from the personal device, for example, based at least in part on received user input indicative of the provided consent. The patient computing entity 102 provides consent to access data of one or more types of activity of the first user such as walking, running, biking, and/or the like, for example, based at least in part on received user input indicative of the provided consent. In some embodiments, the patient computing entity 102 provides consent to access data obtained from one or more additional devices associated with the first user, for example, based at least in part on received user input indicative of the provided consent. For example, the one or more personal devices can include and/or may be associated with a smart watch, a fitness tracker, smart clothing, or any other devices connected to the personal device and capable of collecting data of the first user. In some embodiments, the first user can manually input personal, medical or environmental data associated with the first user. As an example, as noted above, the first user's personal device may be configured for executing an application for recording manual data entry indicative of the first user's food consumed, and such data may be provided and/or recorded by the application.

In some embodiments, the patient computing entity 102 provides consent to access and record one or more most recent phone calls of the personal device of the first user, for example, based at least in part on received user input indicative of the provided consent. In some embodiments, the patient computing entity 102 provides consent to access and record data of recent locations and paths taken by the first user, for example, based at least in part on received user input indicative of the provided consent. Additionally, the patient computing entity 102 provides consent to access and record one or more of recent pictures, video files, or audio files on the personal device of the first user, for example, based at least in part on received user input indicative of the provided consent. For example, an audio file including sounds of a crash or sounds that indicate certain activities such as water skiing can be used to determine what has happened to a patient prior to the medical emergency. In some embodiments, the patient computing entity 102 provides consent to access and record one or more environmental data, for example, based at least in part on received user input indicative of the provided consent. The environmental data can include one or more events accessed from first user's calendar or GPS data on the personal device. The patient computing entity 102 can store the recorded data locally within a memory of the personal device of the first user. Alternatively, the patient computing entity 102 can transmit the recorded data to a cloud storage associated with the patient computing entity 102 for storage in a patient profile associated with the patient (e.g., associated with a patient identifier). In some embodiments, the patient computing entity 102 is configured to receive user input specifying a duration of time in which the recorded data is stored, e.g., a duration of a rolling window of a specified time period. As an example, the rolling window may be identified to encompass the last one or more hours (e.g., 2 hours, 3 hours, 4 hours, 1 day, 1 week, and/or the like). The recorded data may be stored for the rolling window locally within a memory onboard the personal device, or alternatively, the personal device, via the installed application, may be configured to transmit the recorded data to an external storage location, such as a cloud-based storage system associated with a central computing entity of the application. The cloud-based storage system may be configured to automatically delete and/or overwrite stale data generated earlier than the beginning of the rolling window.

In some embodiments, the patient computing entity 102 determines a level of anonymity attached to the recorded data. The patient computing entity 102 determines whether full details of the first user can be recorded. For example, the patient computing entity 102 may determine whether the first user's full name, phone number, address, SSN, or medical ID can be recorded. Alternatively, in some embodiments, the patient computing entity 102 determines whether visually identifiable details of the first user, e.g., 5 ft 4 female, blond hair, brown eyes, 130 lbs., can be recorded. In some embodiments, the patient computing entity 102 determines whether partial details of the first user can be recorded. For example, the patient computing entity 102 may determine whether first user's first name, home city/state, or allergies can be recorded.

In some embodiments, the patient computing device 102 determines one or more conditions for which satisfaction would override, or pause, the data computing entity 106 from recording data (or deleting data) of the first user. In some embodiments, the patient computing entity determines that under certain circumstances, such as during instances in which the first user is participating in particular activities, e.g., exercising, intermittent fasting for a medical test, the user's monitored medical data is expected to violate one or more of the ranges. Such embodiments would result in inaccurate recorded data, which would further mislead the medical practitioners in evaluating first user's medical conditions. For example, the patient computing entity 102 can determine when the first user enters a gym facility to workout, the data computing entity 106 pauses recording data. Additionally, in some embodiments, the patient computing entity 102 determines one or more actions, e.g., driving, or one or more locations, e.g., a gym, or proximity to specific people or places, e.g. to a medical laboratory, that would pause the recording data.

At step/operation 402 the patient computing entity 102 receives user input providing consent to access the recorded data generated at the personal device to an authorized user. To that end, in some embodiments, the patient computing entity 102 (e.g., based at least in part on user input) determines authorized users who would access the recorded data. The authorized users may include medical professionals such as EMTs, doctors and nurses, and others including bystanders, good Samaritans, family members, and friends. In some embodiments, the patient computing entity 102 further determines one or more conditions occurrence of which triggers recording data. Once the one or more conditions are satisfied, the data computing entity 106 starts recording the data. As a non-limiting example, the data computing entity 106 starts recording data of the first user when the first user is traveling 200 miles from home and they have not used their personal device for the last 90 minutes, or when they were driving and an EMT has been within 20 feet for more than 5 minutes. In some embodiments, the patient computing entity 102 determines one or more thresholds and target values that would indicate anomalies specific to the first user. The one or more thresholds can be determined subjectively and for a specific first user. For example, when historically the first user's blood pressure is low, a blood pressure above 95/88 would be an anomaly for that user. In some embodiments, the first user can optionally consent to access and record additional types of data after initial set up. Alternatively, the first user can retract a consent to access and record one or more types of data after initial set up. The first user can further add or remove personal, medical or environmental data at any time after the initial set up.

b. Recording Data of the First User

At step/operation 403 the data computing entity 106 maintains a rolling recording of data generated at the personal device of the first user. In other words, the application begins to record data consented by the first user. Alternatively, in some embodiments, the patient computing entity 102 maintains a rolling recording of data generated at the personal device of the first user. The patient computing entity 102 further stores the recorded data locally. In some embodiments, the patient computing entity 102 transmits the recorded data to the data computing entity 106. As mentioned, the data computing entity 106 records a rolling window of recent data generated at the personal device. In some embodiments, the recent data includes medical data. Alternatively, in some embodiments, recent data for recording includes environmental data. The recorded personal data is selected by the first user of the personal device, and includes recent medical, personal, and environmental data in association with the first user. For example, if the first user selects recording data indicative of the first user's heartbeats, then the heartbeat data (e.g., collected from a heartrate monitor in association with the personal device, such as generated by a wearable device) is recorded. The rolling recording encompasses data generated during a defined duration of time. As noted above, the first user selects the duration of time the rolling recording of the data should be maintained. Moreover, in certain embodiments, various configurations enable a user to provide user input specifying multiple durations of time for recording data, with each of the multiple durations of time corresponding to a particular type of data. In other embodiments, a single duration of time is utilized for recording data of all data types. As a non-limiting example, the first user selects that their heartbeat should be recorded for 3 hours. In some embodiments, the rolling recording of data is characterized by one or more first recording criteria. The first recording criteria may be data type specific, or general across a plurality of data types. In some embodiments, the one or more first recording criteria includes a deviation in blood pressure from a first range. In some embodiments, the one or more first recording criteria includes a deviation in heart rate from a second range. Alternatively, in some embodiments, the one or more first recording criteria includes a deviation in body temperature from a third range. In some embodiments, the one or more first recording criteria includes a deviation in an adrenaline level from a fourth range. In some embodiments, the one or more first recording criteria includes a deviation in a voice tone from a fifth range. In some embodiments, the one or more first recording criteria includes a deviation in a breathing pattern from a sixth range. In some embodiments, the one or more first recording criteria includes a detection of one or more panic words. In some embodiments, the one or more panic words include words indicative of fear, horror, or shock. In some embodiments, the one or more panic words include words indicative of a pain.

In some embodiments, one or more sensors of the personal device of the first user are accessed to collect personal, medical, or environmental data associated with the first user. Additionally, in some embodiments, once the duration of time specified by the first user lapses, e.g., the rolling window lapses, the data computing entity 106 deletes the oldest recorded data, i.e., portions of the recorded data which are recorded first. For example, if the first user determines a rolling window of 2 hours, once the 2-hour rolling window is lapsed, the patient computing entity 102 replaces the oldest recorded data, i.e., the portions of data which were recorded at the beginning of the rolling window, with new recorded data. This "first in-first out" process continues to ensure that there is a 2-hour recorded data available at any time. In some embodiments, the personal device of the first user includes a wearable device capable of measuring data associated with the first user. In some embodiments, the personal device of the first user includes a smartphone capable of measuring data associated with the first user.

In some embodiments, the patient computing entity 102 records the personal data obtained from an accelerometer or a pedometer on the device of the first user. In some embodiments, the patient computing entity 102 records the personal data obtained from a GPS system on the personal device of the first user. In some embodiments, the patient computing entity 102 records the personal data obtained from a smartwatch, or a fitness tracker, coupled to the device of the first user. In some embodiments, the patient computing entity 102 records the personal data obtained from a smart clothing coupled to the device of the first user. For example, the patient computing entity 102 can record one or more phone calls or text messages on the device of the first user. Alternatively, the patient computing entity 102 can record one or more pictures, video or audio files on the device of the first user.

In some embodiments, the data computing entity 106, i.e., the application, records the data generated at the personal device of the first user. The data computing entity 106 may store the recorded data locally on the personal device of the first user. Alternatively, in some embodiments, the patient computing entity 102 records the data generated at the personal device of the first user. The patient computing entity 102 may store the recorded data locally on the personal device of the first user. In some embodiments, the patient computing entity 102 transmits the locally stored recorded data to the data computing entity 106.

c. Transmitting the Recorded Data to Authorized Users

In some embodiments, the data computing entity 106 monitors for a request to access the recorded data. The request can include authorization credentials associated with the second device. The request may further include information associated with the first user, e.g., a name of the first user, visual information to identify the first user, etc. The data computing entity 106 may monitor requests to access the recorded data via a device-to-device short range communication such as a Bluetooth connection, a near field connection (NFC) or a beacon. Such configurations may comprise searching, such as including the detection of authorized devices via communicating with nearby devices. In some embodiments, the data computing entity 106 monitors for a device associated with an authorized user in a proximity of the personal device via one or more of a Bluetooth connection, a NFC, a beacon, etc.

In some embodiments, the data computing entity 106 receives a request to access the recorded data from a second device. In some embodiments, the second device is associated with a medical practitioner. As a non-limiting example, the second device can be associated with an EMT which is helping the first user in a medical emergency. As another non-limiting example, the second device can be associated with a doctor. In some embodiments, the second device is associated with a second user which is designated by the first user (e.g., based at least in part on user input provided during a setup process, as discussed herein). As a non-limiting example, the second device can be associated with a friend or a family member of the first user. As mentioned, during the step/operation 402, the first user can authorize the friend or the family member of the first user to access the first user's recorded data. For security reasons and/or to comply with the regulations, the second device should be authorized to access the recorded data of the first user. Thus, in some embodiments, the request includes authorization credentials associated with the second device.

At step/operation 404, the data computing entity 106 provides access to an authorized device, to the recorded data generated at the personal device of the first user. Access is provided upon verification that the authorization credentials are associated with an authorized user. In some embodiments, the data computing entity 106 may display the recorded data to the second user. In some embodiments, the data computing entity 106 monitors for inbound requests to access the recorded data. For example, the EMT or other medical professional requests access to recorded data from their device, i.e., the second device. The data computing entity 106 receives the request from the second device. In some embodiments, the request is received directly from the second device. In such embodiments, the data computing entity 106 evaluates if requesting party is authorized and transmits the recorded data upon a determination that the second device is an authorized device. In some embodiments, the data computing entity 106 receives the request via the cloud storage. In such embodiments, the data computing entity 106 determines whether the request includes the authentication credentials associated with an authorized user. To provide recorded data associated with a proper patient, the data computing entity 106 further determines whether the request received from the cloud storage includes information identifying the first user. Upon determination that a correct first user, i.e., patient, is identified, the data computing entity 106 transmits the recorded data to the authorized user, i.e., the second device. In some embodiments, the data computing entity 106, upon determination that an authorized personal device is in a proximity of the personal device of user which requires medical attention, transmits first user's information to the authorized personal device. The transmitted information may identify the first user and inform the authorized personal device that the first user is in the proximity of the authorized personal device and requires medical attention.

In some embodiments, the data computing entity 106 notifies the second device that the recorded data is available. In some embodiments, the data computing entity 106 notifies the second device via an application which is executing on the second device. For example, upon notifying the second device, a message pops up on a user interface associated with the application on the second device, indicative of recorded data availability. In some embodiments, the data computing entity 106 sends a message to the second device. As a non-limiting example, the message may include "Medical recorded data is available, [View] [Cancel]". The data computing entity 106 may prompt the second device to either view the recorded data or cancel displaying the recorded data. In some embodiments, the data computing entity 106 detects and stores any time an authorized user accesses, i.e., views, the recorded data.

Alternatively, in some embodiments, the data computing entity 106 proactively searches for authorized devices. The search may include detecting the authorized devices via communicating with nearby devices. In some embodiments, the data computing entity 106 may determine that a device in proximity of the personal device is associated with an authorized user, such as an EMT or a doctor, via one or more of a Bluetooth connection, a near field connection (NFC), a beacon, etc. In other words, the communications between the personal device and the second device can be performed via a device to device short range communication. In some embodiments, geofences acts as a trigger for providing recorded data from a personal device or from a cloud. In some embodiments, the determination that whether a second device is an authorized device is performed by communicating with a server associated with a healthcare provider. Alternatively, in some embodiments, the data computing entity 106 includes a database which contains a list of authorized users. In such embodiments, the determination that whether a second device is an authorized device is performed locally.

In some embodiments, one or more data computing entities associated with one or more patients determine that an authorized personal device is in a proximity of personal devices of the one or more users which require medical attention. In such embodiments, the one or more data computing entities transmit a corresponding first user's information to the authorized personal device. The transmitted information may identify the first user and inform the authorized personal device that the first user is in the proximity of the authorized personal device and requires medical attention.

At step/operation 405, the authorized device evaluates the recorded data. The authorized device may evaluate necessary steps for treatment of the first user. In some embodiments, the patient computing entity 102 determines an authorized user and transmits the recorded data, which is stored locally on the personal device of the first user, to the authorized user directly via any suitable local device-to-device communication method such as Bluetooth, NFC, a beacon, etc. Alternatively, the authorized device evaluates the recorded data which is transmitted to the authorized device. In such embodiments, the recorded data is transmitted to the first user's account on the cloud storage, and the authorized device accesses the recorded data via the cloud storage. In some embodiments, the communications between at least two of the data computing entity 106, the patient computing entity 102, and the authorized personal device are encrypted for added security and privacy.

FIG. 5 provides an example process 500 for sharing the recorded data with a second device, in accordance with some embodiments. FIG. 6 provides an operational example of sharing medical data between a personal device of a first user and a second device. Referring now to FIG. 5, the process 500 begins at step/operation 501 when the data computing entity 106 detects a beacon coupled to the second device (or a user of the second device) within a predetermined proximity from the personal device of the first user. The beacon can be implemented in a hardware form in and/or associated with the second device. Alternatively, the beacon can be implemented in a software form in the second device. For example, the data computing entity 106 detects a beacon within 10 feet from the personal device of the first user. The data computing entity 106 may proactively monitor presence of a beacon associated with an authorized device. In some embodiments, a beacon associated with an authorized device communicates with the personal device of the first user through any suitable method such as Bluetooth or other wireless communication methodologies. In some embodiments, data computing entity 106 receives communications from the beacon and detects that there is an authorized device in a vicinity of the personal device of the first user. In some embodiments, the data computing entity 106 notifies the second device that the recorded data associated with the first user's personal device is available. In various embodiments, the data computing entity 106 provides identifying data regarding the first user to the second device together with an indication that the medical data is available, as illustrated by FIG. 6. For example, the identifying data may comprise a name, a photo, relative size of the first user (e.g., height, weight, etc.), any easily identifiable markings (e.g., tattoos, birth marks, etc.), such that the user of the second device may correlate the medical data provided by the first device with a particular individual. In some embodiments, the data computing entity 106 sends a message to the second device and prompts the second device to either view the recorded data or cancel displaying the recorded data. In some embodiments, the data computing entity 106 detects and stores any time an authorized second user accesses, i.e., views, the recorded personal data.

At step/operation 502, the data computing entity 106 determines whether the beacon is associated with an authorized user. In some embodiments, the data computing entity 106 looks up the beacon in a trusted provider's directory. For example, the data computing entity 106 can look up via an API called from the personal device of the first user which is associated with a healthcare provider to determine whether the beacon is associated with an authorized user. In some embodiments, the beacon can reveal that the beacon is associated with an authorized medical practitioner, e.g., a doctor, an EMT, or a nurse. In some embodiments, the data computing entity 106 includes a database which contains a list of authorized users. In such embodiments, the determination that whether a second device is an authorized is performed locally. In some embodiments, a friend or a family member (or other specifically identified individual) of the first user is identified on the personal device of the first user. Alternatively, in some embodiments, the friend or the family member (or other specifically identified individual) of the first user is identified in the cloud storage. The friend or family member (or other specifically identified individual) of the first user are designated as authorized users by the first user providing user input to the application executing on the patient device 102. In such embodiments, a determination of whether a particular user is authorized may comprise determining whether identifying data associated with the user (e.g., the user requesting access from a second computing device) is represented within a listing of authorized users as generated based at least in part on user input of the patient designating one or more authorized users.

By contrast, medical professionals need not be specifically identified by the patient to enable access to the patient's stored data, and authorization of medical professionals to access the personal data of the patient may encompass a determination of whether the user provides authorization credentials indicating the user is trained and/or licensed as a healthcare professional. In some embodiments, the medical practitioner's personal device transmits data indicative of at least one of a license number associated with the medical practitioner, or an identifier associated with the medical practitioner. In some embodiments, the data computing entity 106 determines whether transmitted data is associated with an authorized device by accessing a database including data of authorized devices. Alternatively, in some embodiments, the data computing entity 106 determines whether transmitted data is associated with an authorized device by accessing an external validation checker entity to determine whether the provided credentials of the medical practitioner indicates that the individual is a qualified care provider to whom the personal data of the patient can be provided. As a non-limiting example, the data computing entity 106 determines whether the transmitted data, which include an employment identifier, is associated with a hospital.

At step/operation 503 the data computing entity 106, upon verification that a user of the second device is an authorized user, transmits the recorded data to the second device. In some embodiments, the data computing entity 106 detects and stores any access to view the recorded data by the authorized users.

At step/operation 504 the data computing entity 106 sends a notification to the second device notifying the user of the second device that the recorded of data is available. The notification can include one or more data describing characteristics of first user that enables the medical practitioner to match the recorded data to the first user.

In some embodiments, an authorized user registers his/her personal device as an authorized device. The authorized user such as a medical practitioner or a caretaker, can register his/her personal device through a designated application associated with the healthcare provider. Alternatively, the authorized user can register his/her personal device through a user account associated with the authorized user on the cloud storage.

With reference to the example configuration illustrated by FIG. 6, in some embodiments, at step/operation 601, the data computing entity 106, e.g., the patient device, receives a data request with authorization credentials from the second device. In some embodiments, the second device is associated with a medical provider. At step/operation 602, the data computing entity 106 receives a request for medical data from the second device. In some embodiments, the data computing entity 106 receives the data request with authorization credentials and the request for medical data simultaneously. Alternatively, in some embodiments, the data computing entity 106 receives the data request with authorization credentials and the request for medical data separately, e.g., in discrete data communications received simultaneously or at different times. At step/operation 603, the data computing entity 106, upon a determination that the second device is an authorized device, transmits data identifying the patient to the second device. In some embodiments, the data computing entity 106 upon receiving the data request with authorization credentials, i.e., step/operation 601, transmits the data identifying the patient to the second device, i.e., step/operation 603. At step/operation 604, the data computing entity 106 transmits patient's medical data within rolling window to the second device. Alternatively, in some embodiments, one or more of the steps/operations 601, 602, 603, and 604 is performed through the cloud storage.

d. Recorded Data Representation

In some embodiments, the data computing entity 106 prioritizes an order of display of the recorded data. The data computing entity 106 prioritizes order of display of the recorded data based on a degree of deviation from at least one of the first range, the second range, the third range, the fourth range, the fifth range, or the sixth range. In some embodiments, the data computing entity 106 provides one or more representation of the recorded data to the second device via a plurality of diagrams, graphs, or charts. The one or more data representations can include line diagrams, graphs or charts; bar diagrams, graphs, or charts; pie diagrams, graphs, or charts, etc. In some embodiments, the data computing entity 106 determines whether each data representation includes a deviation from one or more user specified thresholds. In such embodiments, the first user, prior to recording the personal data, determines a threshold for each of the first range, second range, the third range, the fourth range, the fifth range, or the sixth range. In some embodiments, the data computing entity 106 may determine whether each data representation includes anomalies, i.e., deviation from a first user's normal trend. In such embodiments, the data computing entity 106 identifies one or more time periods during which the recorded data deviates from a normal trend. In some embodiments, the data computing entity 106 moves each data representation with anomalies or threshold violations to a top of the list which is reported to the second device. In some embodiments, the data computing entity 106 moves one or more data representations with highest variations higher to the top of the display, i.e., prioritizes the most relevant charts by placing them at the top of the list. In some embodiments, the data computing entity 106 combines one or more data representations based on similarity or relevancy. As a non-limiting example, for each chart that has anomalous recorded data with compatible x axis range, the data computing entity 106 combines the charts into a single chart. This combining of charts reduces overall number of charts that the medical practitioner needs to go through, which can save a time to respond to a medical emergency.

In some embodiments, the data computing entity 106 correlates events and recorded personal data. The data computing entity 106 may correlate data to show common events, spikes, anomalies, trends, activities or data readings that are in common with other data or conditions. For example, the data computing entity 106 detects one or more spikes in the recorded data that correspond on the horizontal, e.g., time, axis. For each correlation, the data computing entity 106 may draw a vertical line. In some embodiments, the data computing entity 106 marks that time segment with a label for each correlation, e.g., adrenaline spike, audible crash indicators, heartrate spike, extreme accelerometer changes, etc. In some embodiments, the data computing entity 106 indicates the names of the first users that had the correlation in data to further reduce a number of graphs or data that the medical practitioner needs to consume.

In some embodiments, the data computing entity 106 highlights timeline events and indicators. The data computing entity 106 may use any suitable method to interpret activities, e.g. cycling, running, etc. In some embodiments, the data computing entity 106 overlays the activities on a graph to further reduce complexity of the recorded data the medical practitioner needs to consume.

In some embodiments, the data computing entity 106 allows the second device to specify a template for the recorded data including at least one of an order, a graph type, one or more colors, or a position.

In some embodiments, the data computing entity 106 queries the second device (or a database) for a profile associated with the user of the second device. If the second user profile exists, the data computing entity 106 reformats the recorded data to match the second user's preferred template. In some embodiments, the data computing entity 106 allows the second device to specify certain conditions that reformats the recorded data to a specified template. The specifying can be performed via voice buttons or pre-configured buttons. As a non-limiting example, when an EMT says "Condition—Shock," the data computing entity 106 reformats data to show graphs and information related to "shock." If data is available, the data computing entity 106 uses the EMT's template for "Shock". As another non-limiting example, when an EMT says "Condition—Cardiovascular," the data computing entity 106 reformats recorded personal data to show graphs and information related to "cardiovascular". Similarly, if data is available, the data computing entity 106 uses the EMT's template for "cardiovascular". As yet another non-limiting example, when an EMT says "Condition—Burn," the data computing entity 106 reformats the recorded personal data to show graphs and information related to "burn". If data is available, the data computing entity 106 uses the EMT's template for "burn". Although discussed in reference to providing such user-specified formatting requirements at the data computing entity 106, it should be understood that in certain embodiments, the user-specified formatting may occur at the second computing device. In such embodiments, data may be provided to the second computing device in an unorganized format, the second device (e.g., via an application executing on the second device) may format the data in accordance with a formatting specification (e.g., a stylesheet) stored at the second device.

FIGS. 7A-7C provides an operational example of a user interface on a personal device of an authorized medical personnel, in accordance with some embodiments. As shown in FIG. 7A, in some embodiments, the data computing entity 106 on the second device determines one or more possible users which match the first user. The authorized medical personnel can determine the first patient, i.e., the first user, and choose the recorded data associated with his/her personal device. As shown in FIG. 7B, upon choosing the correct patient from among the one or more possible users by the medical personnel, the data computing entity 106 indicates what sort of recorded data, i.e., medical data, personal data, or environmental data, is available. As shown in FIG. 7C, in some embodiments, the data computing entity 106 displays one or more prioritized recorded data based on the deviation from the thresholds or severity of the conditions.

It should be understood that identifying relevant data to be provided to the second user device may be performed via any of a variety of methodologies. As another non-limiting example, rather than using proximity detection between the first user and the second user, the recorded data associated with the first user may be accessed (e.g., from a cloud-based storage system) based at least in part on a request generated by the second device and including identifying data of the first user obtained by scanning a first identification (e.g., a driver's license, a passport, and/or the like). Alternatively, in some embodiments, the recorded data is accessed by scanning a QR code associated with the first user. In some embodiments, the recorded data is stored in the personal device of the first user. Alternatively, in some embodiments, the recorded data is sent and stored in a cloud storage. In such embodiments, the second device accesses the recorded data through the cloud storage.

Example 1

As a non-limiting example, a person is involved in a car accident, which at first impression may have caused by driver's mistake. The EMT approaches an unconscious patient in one vehicle and triggers a release of the last 2 hours of recorded medical data associated with the patient. The recorded medical data indicates that the patient was having irregular heartbeat with a high breathing rate prior to the accident. The recorded medical data shows that the patient had recently been speaking with a person with a number in the patient's address contact list. Because the EMT is an authorized user, he/she can contact the last called person and discovers that the patient was complaining of chest pains and was trying to drive him/herself to a hospital. In this case, cause of the accident can be determined. Moreover, the patient can be treated quickly and acutely for the condition at hand.

Example 2

As another non-limiting example, an employee is found unconscious in a kitchen of a restaurant in a walk-in freezer. The employee has a slightly cool body temperature and a very slow heart rate. A reasonable assessment by a medical practitioner may be that hypothermia is one of the causes of the employee's conditions. However, recorded data show that that employee was subjected to intense heat an hour before and had spent most of the day by a loading dock. Other sensor readings are conducive to heat stroke. Another person confirms this employee was outside unloading large boxes for hours which is backed by the medical recorder data showing the location of the employee and outside temperatures exceeding 95 degrees. The employee being diabetic, also showed a sharp reduction in glucose. The employee is treated with the knowledge that a heat stroke caused the employee's initial issues and he had apparently retreated to the walk-in freezer to try to cool off. These recorded medical data change the triage result of the employee and he/she is treated more effectively and safely.

Example 3

As yet another non-limiting example, an EMT arrives at the scene of an accident and sees two damaged vehicles and two injured persons. A first patient is in shock and a second patient is unconscious. Upon first glance, it looks like the second patient may have been in a vehicle, but after receiving the recorded medical data for the second patient the EMT sees that the second patient's recorded medical data is indicative to a person exercising or riding a bike recently. Further review of the scene of the accident reveals a damaged bike in the bushes which indicates a variation in treatment possibly due to more serious internal injuries considering the impact.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for sharing medical data of a first user generated in association with a personal device of the first user, the computer-implemented method comprising:
    maintaining identifying data of the first user in association with the personal device of the first user;
    maintaining a rolling recording of medical data generated via one or more sensors in association with the personal device of the first user, wherein medical data is temporarily maintained within the rolling recording for a defined duration of time after the medical data is generated and the medical data is removed from the rolling recording upon expiration of the defined duration of time and wherein the medical data temporarily maintained within the rolling recording comprises data reflecting content of manual user input provided by the first user to the personal device of the first user;
    receiving a request to access the medical data within the rolling recording from a second device associated with a second user and determined to be within a defined range of the personal device of the first user, wherein the request comprises authorization credentials associated with the second device and the second user;
    upon verification that the authorization credentials are associated with an authorized user, providing, to the second device, the identifying data of the first user; and
    upon detecting a request to access the rolling recording of medical data generated in association with the personal device of the first user, providing, to the second device, access to the rolling recording of medical data generated in association with the personal device of the first user.

2. The computer-implemented method of claim 1, wherein the authorization credentials comprise data identifying a user of the second device as at least one of: one or more persons designated by the first user or a medical professional.

3. The computer-implemented method of claim 1, wherein the rolling recording of medical data is characterized by one or more first criteria comprising at least one of: a detection of one or more panic words, and a deviation in at least one of: a blood pressure from a first range, a heart rate from a second range, a body temperature from a third range, an adrenaline level from a fourth range, a voice tone from a fifth range, and a breathing pattern from a sixth range.

4. The computer-implemented method of claim 3, further comprising:
    upon providing access to the rolling recording of medical data to a second device, providing data identifying a prioritization of display of the recorded medical data based on a degree of deviation from at least one of: the first range, the second range, the third range, the fourth range, the fifth range, and the sixth range.

5. The computer-implemented method of claim 1, wherein receiving a request to access the medical data from a second device comprises:
    detecting a beacon coupled to the second device within a pre-determined proximity from the device of the first user;
    determining whether the beacon is associated with an authorized user;
    upon verification that a user of the second device is an authorized user, transmitting the rolling recording of medical data to the second device; and
    sending a notification to the second device notifying the user of the second device that the rolling recording of medical data is available.

6. The computer-implemented method of claim 1, wherein the medical data comprises data generated by the personal device of the first user and data generated by a wearable device in electronic communication with the personal device of the first user.

7. The computer-implemented method of claim 6, wherein the medical data comprises a recording of one or more phone calls or messages during the defined duration of time.

8. An apparatus for implementing sharing medical data of a first user generated in association with a personal device of the first user, the apparatus comprising one or more processors and at least one non-transitory memory storage area, the apparatus configured to:
    maintain identifying data of the first user in association with a personal device of the first user;
    maintain a rolling recording of medical data generated via one or more sensors in association with the personal device of the first user, wherein medical data is temporarily maintained within the rolling recording for a defined duration of time after the medical data is generated and the medical data is removed from the rolling recording upon expiration of the defined duration of time and wherein the medical data temporarily maintained within the rolling recording comprises data reflecting content of manual on user input provided by the first user to the personal device of the first user;
    receive a request to access the medical data from a second device associated with a second user and determined to be within a defined range of the personal device of the first user, wherein the request comprises authorization credentials associated with the second device; and
    upon verification that the authorization credentials are associated with an authorized user, provide, to the second device, the identifying data of the first user; and
    upon detecting a request to access the rolling recording of medical data generated in association with the personal device of the first user, provide, to the second device, access to the rolling recording of medical data generated in association with the personal device of the first user.

9. The apparatus of claim 8, wherein the authorization credentials comprise data identifying a user of the second device as at least one of: one or more persons designated by the first user or a medical professional.

10. The apparatus of claim 8, wherein the rolling recording of medical data is characterized by one or more first criteria comprising at least one of: a detection of one or more panic words, and a deviation in at least one of: a blood pressure from a first range, a heart rate from a second range, a body temperature from a third range, an adrenaline level from a fourth range, a voice tone from a fifth range, and a breathing pattern from a sixth range.

11. The apparatus of claim 10, further comprising:
upon providing access to the rolling recording of medical data to a second device, provide data identifying a prioritization of display of the recorded pre-determined data based on a degree of deviation from at least one of: the first range, the second range, the third range, the fourth range, the fifth range, and the sixth range.

12. The apparatus of claim 8, wherein to receive a request to access the medical data from a second device the apparatus is further configured to:
detect a beacon coupled to the second device within a pre-determined proximity from the device of the first user;
determine whether the beacon is associated with an authorized user;
upon verification that a user of the second device is an authorized user, transmit the rolling recording of medical data to the second device; and
send a notification to the second device notifying the user of the second device that the rolling recording of medical data is available.

13. A computer program product comprising a non-transitory computer readable medium having computer program instructions stored therein, the computer program instructions when executed by a processor, cause the processor to:
maintain identifying data of a first user in association with a personal device of the first user;
maintain a rolling recording of medical data generated via one or more sensors in association with the personal device of the first user, wherein medical data is temporarily maintained within the rolling recording for a defined duration of time after the medical data is generated and the medical data is removed from the rolling recording upon expiration of the defined duration of time and wherein the medical data temporarily maintained within the rolling recording comprises data reflecting content of manual user input provided by the first user to the personal device of the first user;
receive a request to access the medical data within the rolling recording from a second device associated with a second user and determined to be within a defined range of the personal device of the first user, wherein the request comprises authorization credentials associated with the second device; and
upon verification that the authorization credentials are associated with an authorized user, provide, to the second device, the identifying data of the first user; and
upon detecting a request to access the rolling recording of medical data generated in association with the personal device of the first user, provide, to the second device, access to the rolling recording of medical data generated in association with the personal device of the first user.

14. The computer program of claim 13, wherein the authorization credentials comprise data identifying a user of the second device as at least one of: one or more persons designated by the first user or a medical professional.

15. The computer program of claim 13, wherein the rolling recording of medical data is characterized by one or more first criteria comprising at least one of: a detection of one or more panic words, and a deviation in at least one of: a blood pressure from a first range, a heart rate from a second range, a body temperature from a third range, an adrenaline level from a fourth range, a voice tone from a fifth range, and a breathing pattern from a sixth range.

16. The computer program of claim 15, further comprising:
upon providing access to the rolling recording of medical data to a second device, provide data identifying a prioritization of display of the recorded pre-determined data based on a degree of deviation from at least one of: the first range, the second range, the third range, the fourth range, the fifth range, and the sixth range.

17. The computer program of claim 13, wherein to receive a request to access the medical data from a second device the computer program is further configured to:
detect a beacon coupled to the second device within a pre-determined proximity from the device of the first user;
determine whether the beacon is associated with an authorized user;
upon verification that a user of the second device is an authorized user, transmit the rolling recording of medical data to the second device; and
send a notification to the second device notifying the user of the second device that the rolling recording of medical data is available.

* * * * *